United States Patent [19]

Leibowitz et al.

[11] 4,435,409

[45] Mar. 6, 1984

[54] METHOD OF STIMULATING PRODUCTION OF IGM ANTIBODIES

[75] Inventors: Mitchell J. Leibowitz, West Nyack, N.Y.; Ah S. Kong, Westfield, N.J.; Paula Sonnino-Goldman, Stamford, Conn.; Peter Wolf, Granite Springs, N.Y.

[73] Assignee: USV Pharmaceutical Corporation, Tarrytown, N.Y.

[21] Appl. No.: 329,160

[22] Filed: Dec. 10, 1981

[51] Int. Cl.³ .......................................... A61K 31/455

[52] U.S. Cl. .................................................. 424/266
[58] Field of Search ........................................ 424/266

[56] References Cited

U.S. PATENT DOCUMENTS 3,485,847 12/1969 Bossert et al. ...................... 424/266

Primary Examiner—Jerome D. Goldberg

[57] ABSTRACT

A new use for nifedipine is provided. The new use is in a method of stimulating production of IgM antibodies in mammals.

6 Claims, No Drawings

METHOD OF STIMULATING PRODUCTION OF IGM ANTIBODIES

BACKGROUND OF THE INVENTION (1) Field of the Invention

The invention relates to a method of stimulating production of IgM antibodies, more particularly, the use of nifedipine in this stimulation.

(2) Background of the Invention

The compound used in the current invention is described in U.S. Pat. No. 3,485,847 assigned to Bayer and is known to be a coronary vasodilator and calcium blocker.

A recently published work by Cerrina et al, Am Rev Respir Dis 1981; 123:156-160 discloses that nifedipine, while not modifying the basic bronchial tone of patients with asthma, does prevent exercise-induced asthma.

Tanizaki et al of Creighton University's Department of Medicine have disclosed that nifedipine can have inhibitory effects on allergic reactions.

SUMMARY OF THE INVENTION

The method of stimulating production of IgM antibodies in mammals comprising administering an effective amount of nifedipine.

DETAILED DESCRIPTION OF THE INVENTION

Nifedipine is a compound having the following structure $$\text{(structure of nifedipine)}$$

Its chemical name is 2,6-Dimethyl-4-(2′nitrophenyl)-3,5 dicarbomethoxy-1,4-dihydropyridine.

The inventors have found that nifedipine affects both humoral and cellular immune processes resulting in the stimulation of the production of IgM antibodies useful in the prevention and treatment of a variety of disorders.

Nifedipine was found to stimulate production of IgM antibodies in mice. The test used to determine this activity was a modification of the method of Jerne and Nordin (Science 140: 405, 1963). The test was as follows:

(1) Administering nifedipine to mice at the time of immunization with sheep red blood cells (used to determine the primary humoral immune response to antigen);

(2) Removing the mice's spleens 5 days after immunization, and (3) Using a hemolytic plaque assay to enumerate the B lymphocytes producing IgM antibodies in vitro.

The following table shows that the control IgM production was potentiated by approximately 125-500% in mice treated with nifedipine, 0.4 to 2 mg/kg by the intraperitoneal route.

| Effect of Nifedipine on IgM Anti-SRBC* Response | | | | |
|---|---|---|---|---|
| | Experiment 1 | | Experiment 2 | |
| Dose Mg/Kg, I.P. | PFC**/$10^6$ ± S.D. | % Potentiation | PFC/$10^6$ ± S.D. | % Potentiation |
| None | 425 ± 273 | | 147 ± 73 | |
| 0.4 | — | | 743 ± 250 | 406 |
| 2 | 966 ± 318 | 127 | 885 ± 587 | 503 |

*SRBC = Sheep Red Blood Cells
**PFC = Plaque Forming Cells

Nifedipine has been found also to selectively inhibit, in vitro, mitogen-stimulated proliferation of mouse splenic lymphocytes. This discovery was made using a modification of a method suggested by Oppenheim and Rosenstreich in *In Vitro Methods in Cell Mediated and Tumor Immunity*, eds. B. R. Bloom and J. R. David, Academic Press, N.Y., 1976.

Two sets of cultures were prepared. In the first set mouse splenocytes were incubated with nifedipine in the presence of Concanavalin A (CON A), a mitogen which stimulates proliferation of T lymphocytes.

The second set of cultures were also mouse splenocytes incubated with nifedipine but in the presence of lipopolysaccharide (LPS) a mitogen which stimulates proliferation of B lymphocytes.

After 40 or 66 hours, both sets of cultures were pulsed with $^3$H-thymidine. The incorporation of radioactivity into the newly synthesized DNA was used as the measure of lymphocyte proliferation.

As summarized in the following table, T lymphocyte stimulation by CON A was inhibited by approximately 60-70% by nifedipine (0.01 and 0.1 μg/ml). This same concentration of nifedipine was essentially nonsuppressive to LPS-induced proliferation of B lymphocytes. Only at high concentrations (10 and 25 μg/ml) were both cell types similarly suppressed and these high levels were shown to be cytotoxic by the trypan blue dye exclusion test.

| Effect of Nifedipine on LPS and CON A Stimulated Murine Spleen Cells | | | | |
|---|---|---|---|---|
| | 3H-Thymidine Incorporation | | | |
| | LPS | | CON A | |
| Concentration (μg/ml) | Counts per Minute | % Inhibition | Counts per Minute | % Inhibition |
| 0 | 96,713 | — | 40,846 | — |
| 25 | 2 | 100 | −178 | 100 |
| 10 | 1,044 | 99 | 207 | 99 |
| 1 | 56,670 | 41 | 3,124 | 92 |
| 0.1 | 95,400 | 1 | 11,828 | 71 |
| 0.01 | 104,116 | 8 | 16,203 | 60 |

The current inventors have found that nifedipine has a useful profile of biological activity because it suppresses T cells but not B cells and stimulates production of IgM. While not being limited by speculation on the mechanism of action of nifedipine in stimulating IgM production, the selective inhibition of T cell proliferation indicated in the above experiment allows the speculation that if T cell inhibition is largely reflecting an effect on T suppressor (Ts) cells, then this could be the basis for enhancement of IgM production by B lymphocytes. It can be postulated from reports by Goldman and Goldblum (Ped. Clin. N. Amer. 24, 277, 1977) and Florentin et al. (in Pharmacology of Immunoregulation, N.Y., Academic Press, 1978) that such actions would be useful in enhancing host resistance ("pro-host" therapy), since synthesis of IgM antibodies constitutes the primary humoral immune response. Therefore, nifedipine is useful as a pro-host therapeutic in preventing and treating a variety of diseases involving antibodies, such as viral infections, bacterial infections, and parasitic/fungal infections, as well as valuable in enhancing the protective action of vaccines. In addition, the activity of nifedipine makes it useful in the treatment of immunodeficiency, whether induced by drugs, X-irradiation or genetically induced. IgM deficiency diseases include, but are not limited by, recurrent infections, sudden unexpected septicemia, and meningitis.

We claim:

1. A method of stimulating production of IgM antibodies in a mammal in need of such IgM antibodies comprising: the administering to said mammal an effective amount of nifedipine to stimulate production of IgM antibodies.

2. The method of claim 1 wherein the nifedipine is administered in unit dosage form.

3. The method of claim 1 wherein the nifedipine is administered to said mammal in a dosage form in a pharmaceutially acceptable diluent.

4. The method of claim 1 wherein the nifedipine is administered orally.

5. The method of claim 4 wherein the nifedipine is a solid dosage form.

6. The method of claim 5 wherein said dosage form is a tablet.

* * * * *